(12) United States Patent
McConnell et al.

(10) Patent No.: US 11,467,163 B2
(45) Date of Patent: Oct. 11, 2022

(54) DETERMINATION OF GLYCOSYLATION SIGNATURE

(71) Applicants: Randox Laboratories Ltd., Crumlin (GB); Randox Teoranta, Donegal (IE)

(72) Inventors: Ivan McConnell, Crumlin (GB); Peter Fitzgerald, Crumlin (GB); John Lamont, Crumlin (GB); Ciaran Richardson, Donegal (IE)

(73) Assignees: Randox Laboratories Ltd., Crumlin (GB); Randox Teoranta, Donegal (IE)

( * ) Notice: Subject to any disclaimer, the term of this patent is extended or adjusted under 35 U.S.C. 154(b) by 266 days.

(21) Appl. No.: 16/065,646

(22) PCT Filed: Dec. 23, 2016

(86) PCT No.: PCT/GB2016/054074
§ 371 (c)(1),
(2) Date: Jun. 22, 2018

(87) PCT Pub. No.: WO2017/109518
PCT Pub. Date: Jun. 29, 2017

(65) Prior Publication Data
US 2019/0004050 A1 Jan. 3, 2019

(30) Foreign Application Priority Data
Dec. 23, 2015 (GB) ..................... 1522839

(51) Int. Cl.
*G01N 33/574* (2006.01)
(52) U.S. Cl.
CPC . *G01N 33/57484* (2013.01); *G01N 33/57438* (2013.01); *G01N 2333/4724* (2013.01); *G01N 2440/38* (2013.01)

(58) Field of Classification Search
None
See application file for complete search history.

(56) References Cited

U.S. PATENT DOCUMENTS

2006/0057634 A1    3/2006  Rye
2009/0246800 A1*  10/2009  Mattingly ........ G01N 33/54326
                                                            435/7.1
2011/0257029 A1*  10/2011  Haab .................. G01N 33/6803
                                                            506/9

(Continued)

FOREIGN PATENT DOCUMENTS

| JP | H7191027 A | 7/1995 |
|----|-----------|--------|
| JP | 2005-527835 A | 9/2005 |
| WO | 2015097863 A1 | 7/2015 |

OTHER PUBLICATIONS

Yue (2009) Mol. Cell. Prot 8:7 p. 1697 (Year: 2009).*

(Continued)

*Primary Examiner* — Rebecca M Giere
*Assistant Examiner* — Xiaoyan Zou
(74) *Attorney, Agent, or Firm* — Gavrilovich, Dodd & Lindsey LLP

(57) ABSTRACT

The present invention describes methods of determining the glycosylation signature and determining the level of a protein in a sample obtained from a patient.

The present invention also describes use of a patient protein glycosylation profile to identify the presence or absence of a disease in subjects.

14 Claims, 13 Drawing Sheets

(56) References Cited

U.S. PATENT DOCUMENTS

2013/0005598 A1    1/2013   Haab et al.
2016/0084844 A1*  3/2016   Nudelman ............. G01N 33/53
                                                          424/185.1

OTHER PUBLICATIONS

Yoshida (2012) PLOS 7:1-12 (Year: 2012).*
Yue (2009) MCP 8.7 p. 1697-1707 (Year: 2009).*
Goncalves et al., "Antigen, antibody and immune complex detection in serum samples from rats experimentally infected with Strongyloides venezuelensis," Experimental Parasitology, 130(3):205-208, Jan. 10, 2012.
Lindberg, Pia, European Patent Office, PCT/GB2016/05474, International Search Report and Written Opinion, 2018.
Ryden et al., "Lectin ELISA for analysis of alpha(1)-acid glycoprotein fucosylation in the acute phase response," Clinical Chemistry, 45(11), 2010-2012, 1999.
Silva, M. Luisa S., "Cancer serum biomarkers based on aberrant post-trasnlational modifications of glycoproteins: Clinical value and discovery strategies," BBA—Reviews on Cancer, 1856(2):165-177, Jul. 30, 2015.
Vuskovic et al., "Processing and analysis of serum antibody binding signals from Printed Glycan Arrays for diagnostic and prognostic applications," International J. of Bioinformatics Research and Applications, 7(4):402, Jan. 2011.
Yue et al.,"The Prevalence and Nature of Glycan Alternations on Specific Proteins in Pancreatic Cancer Patients Revealed Using Antibody-Lectin Sandwich Arrays," Mol. & Cellular Proteomics, 8(7):1697-1707, 2009.

* cited by examiner

Format 1 (Chips 3 to 9 are optional)
Chip 1 for the detection of protein(s) at discrete test regions (DTRs)
Chips 2 to 7 for the detection of up to 6 different glycans on protein(s) at DTRs
Chip 8 spotted proteins for the detection of autoantibodies to protein(s) at DTRs
Chip 9 spotted glycans for the detection of autoantibodies to glycan residue(s) at DTRs Format 2 (Chips 3 to 9 are optional)
Chip 1 for the detection of protein(s) (total protein) at discrete test regions (DTRs)
Chips 2-7 for the detection of up to 6 different glycans on protein(s) at DTRs
Chip 8 spotted proteins for the detection of autoantibodies to protein(s) at DTRs
Chip 9 spotted glycans for the detection of autoantibodies to glycan residue(s) at DTRs

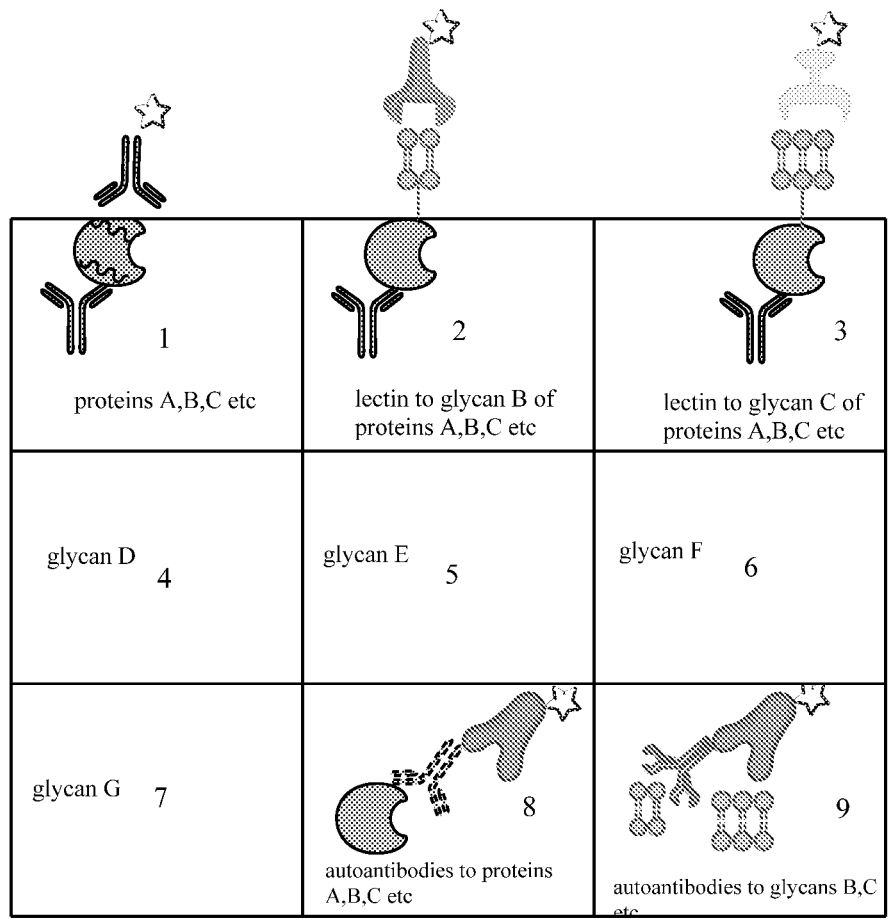

 protein A 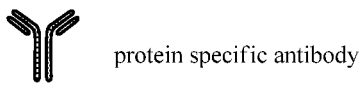 protein specific antibody  lectin X

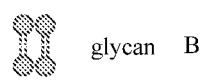 glycan B 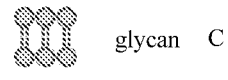 glycan C  lectin Y

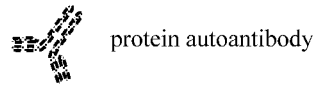 protein autoantibody 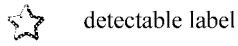 detectable label 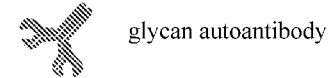 glycan autoantibody

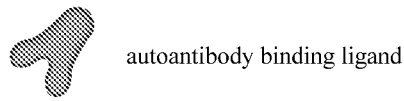 autoantibody binding ligand 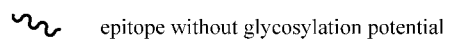 epitope without glycosylation potential

Figure 2

Format 3 (Chips 3 and 4 are optional)
Chip 1 for the detection of protein(s) at discrete test regions (DTRs)
Chip 2 for the detection of different glycans (on different proteins) at DTRs on a single chip
Chip 3 spotted proteins for the detection of autoantibodies to protein(s) at DTRs
Chip 4 spotted glycans for the detection of autoantibodies to glycan residue(s) at DTRs

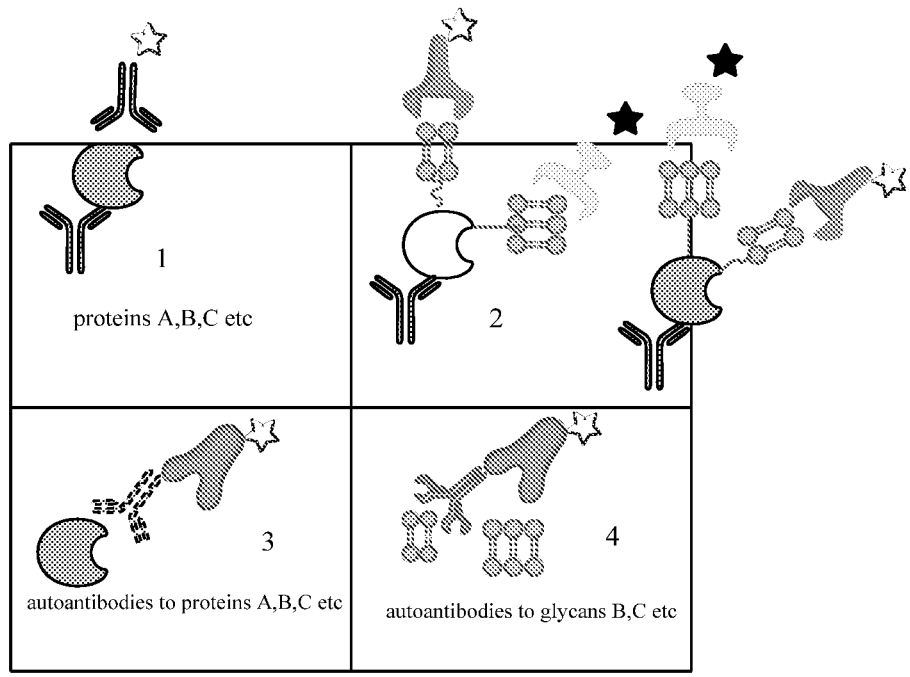

 protein B   Flurophore 1   Fluorophore 2

 protein A   autoantibody binding ligand   lectin X

 glycan B   glycan C   lectin Y

 protein autoantibody   glycan autoantibody

 protein specific antibody

Figure 3

Format 4 (Chips 3 and 4 are optional)
Chip 1 for the detection of protein(s) (total protein) at discrete test regions (DTRs)
Chip 2 for the detection of different glycans (on different proteins) at DTRs on a single chip
Chip 3 spotted proteins for the detection of autoantibodies to protein(s) at DTRs
Chip 4 spotted glycans for the detection of autoantibodies to glycan residue(s) at DTRs

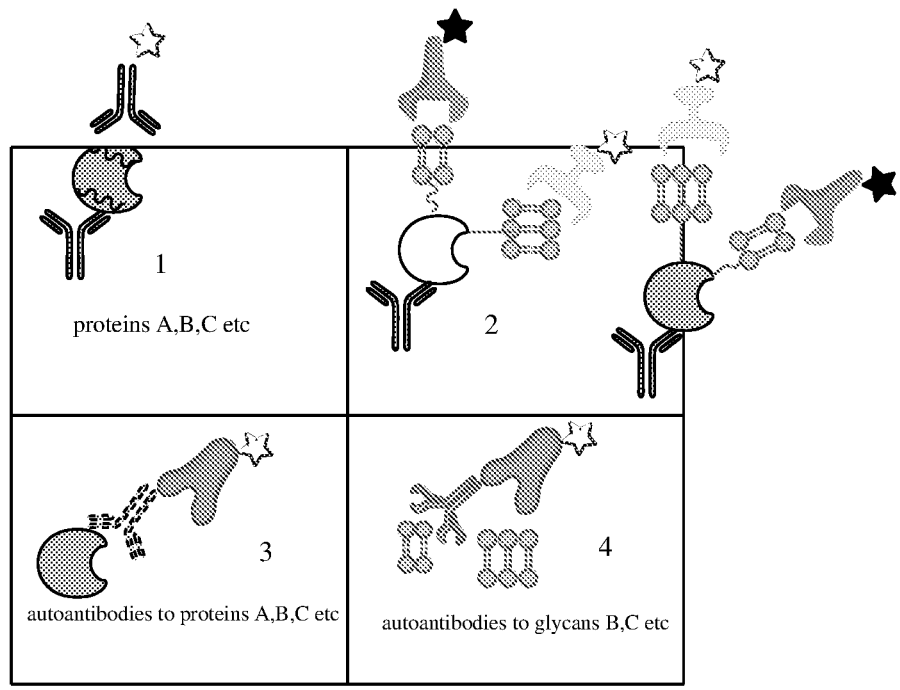

 protein B   Flurophore 1   Fluorophore 2

 protein A   protein specific antibody   lectin X

 glycan B   glycan C   lectin Y

 protein autoantibody   glycan autoantibody

 autoantibody binding ligand   epitope without glycosylation potential

Figure 4

Format 5
Single Chip with antibodies spotted at DTRs - can capture a single protein e.g. protein 1 or multiple proteins e.g. proteins 1 & 2. The Format enables measurement of glycans and total protein(glycosylated & unglycosylated) on a single Chip. Although only total protein and dual glycan detection is exemplified, further glycans may be detected using lectins labeled with further discriminating flurophores.

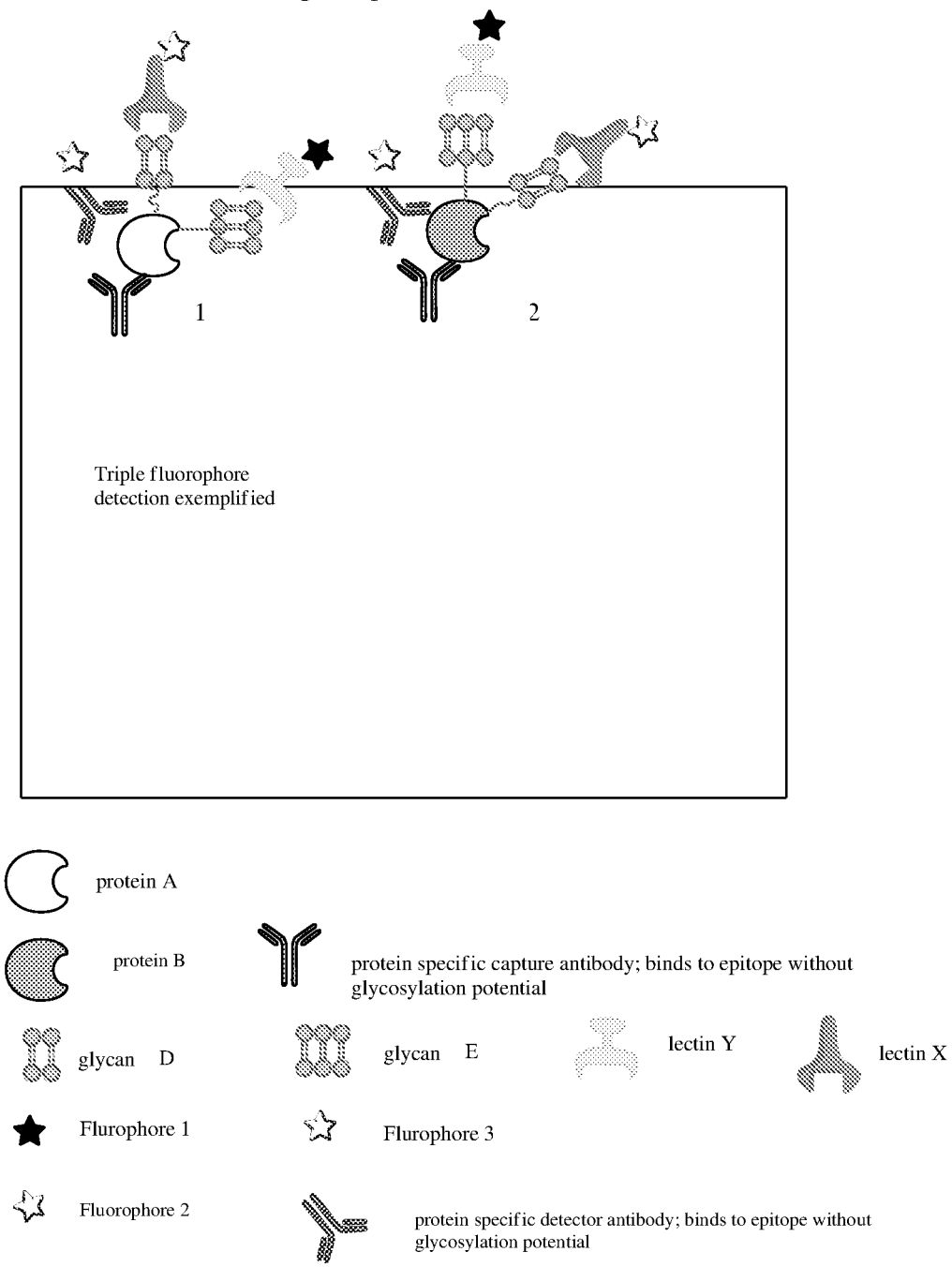

Figure 5

Format 6
Single Chip with antibodies spotted at DTRs - can capture a single protein e.g. protein 1 or multiple proteins e.g. proteins 1 & 2. The Format enables measurement of protein glycosylation signature.

Format 7
Single Chip with antibodies spotted at DTRs - can capture a single protein e.g. protein 1 or multiple proteins e.g. proteins 1 & 2. The Format enables measurement of unglycosylated protein and glycosylated protein.

Format 8 (Chips 3 to 8 are optional)
Chip 1 for the detection of protein(s) (total protein) at discrete test regions (DTRs)
Chips 2-7 for the detection of up to 6 different glycans on protein(s) at DTRs
Chip 8 spotted proteins for the detection of autoantibodies to protein(s) at DTRs
Chip 9 for the detection of unglycosylated protein(s) at DTRs

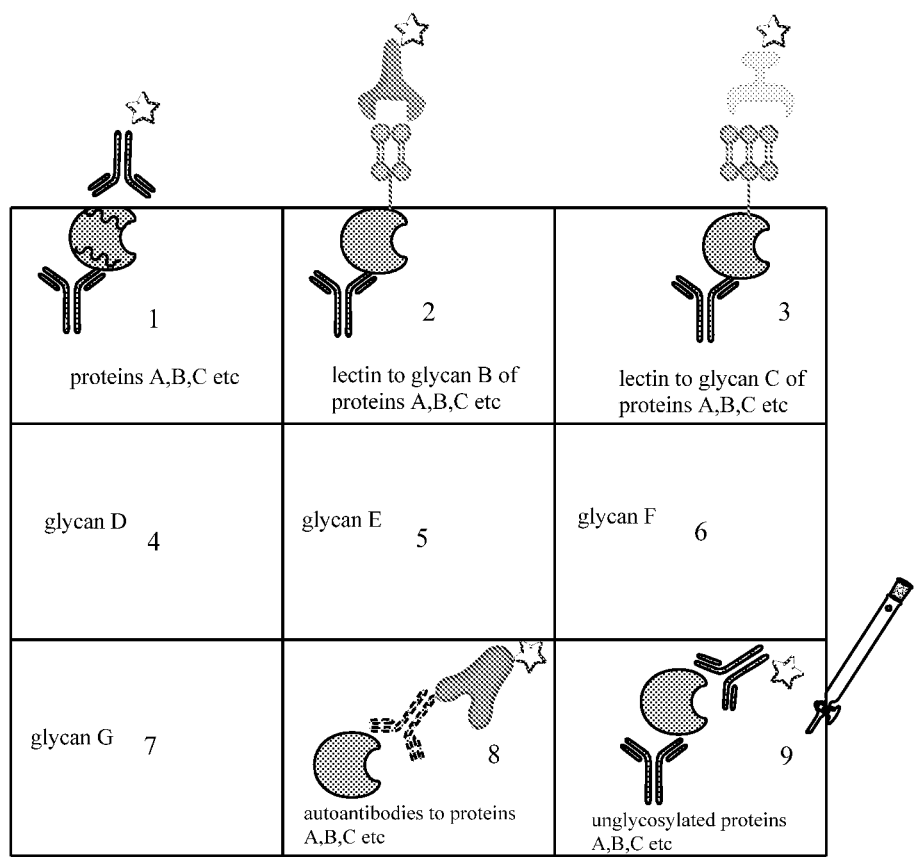

 protein A   protein specific antibody   lectin X

 glycan B   glycan C   lectin Y

 autoantibody binding ligand   detectable label

 protein autoantibody

  epitope without glycosylation potential sample subjected to glycosylated protein depletion prior to addition to chip

Figure 8

Format 9 (Chips 3 to 8 are optional)
Chip 1 for the detection of protein(s) at discrete test regions (DTRs)
Chips 2-7 for the detection up to 6 different glycans on protein(s) at DTRs
Chip 8 spotted proteins for the detection of autoantibodies to protein(s) at DTRs
Chip 9 for the detection of unglycosylated protein(s) at DTRs

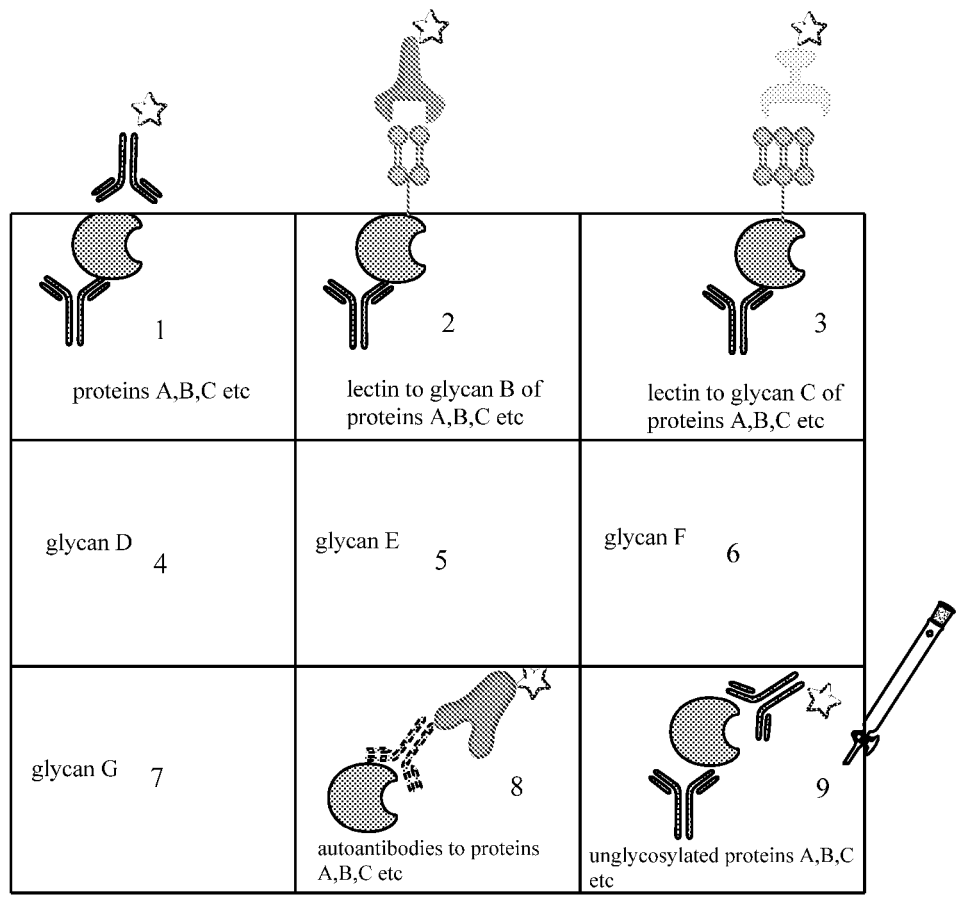

 protein A   protein specific antibody   lectin X

 glycan B   glycan C   lectin Y

 protein autoantibody   detectable label

 autoantibody binding ligand   sample subjected to glycosylated protein depletion prior to addition to chip

Figure 9

DETERMINATION OF GLYCOSYLATION SIGNATURE

CROSS REFERENCE TO RELATED APPLICATION

This application is a U.S. National Stage Application filed under 35 U.S.C. § 371 and claims priority to International Application No. PCT/GB2016/054074, filed Dec. 23, 2016, which application claims priority to Great Britain Application No. 1522839.9, filed Dec. 23, 2015, the disclosures of which are incorporated herein by reference in their entireties.

FIELD OF THE INVENTION

This invention relates to methods of determining the glycosylation signature and determining the level of a protein in a sample. The invention is also directed to use of a patient protein glycosylation profile to identify the presence or absence of a disease in subjects.

BACKGROUND OF THE INVENTION

Many proteins are glycosylated after translation. This post-translational modification involves chemical attachment of sugars to a protein by glycosidic bonds to yield a glycoprotein. Protein glycosylation may take a number of forms and is defined according to the type of glycosidic bonds that occur.

N-linked glycosylation involves attachment of a sugar molecule to the nitrogen (N4) atom in the side chain of an Asparagine residue within the consensus sequence Asn-Xaa-Ser/Thr (where Xaa is not Proline). This modification occurs in secreted and membrane proteins of eukaryotes and archea, and it is absent in bacteria. This process begins co-translationally in the endoplasmic reticulum, where preassembled blocks of 14 sugars (including 2 N-acetylglucosamines, 9 mannoses and 3 glucoses) are added to the nascent polypeptide chain. After cleavage of 3 glucose and 1 mannose residues, the protein is transferred to the Golgi apparatus where the glycans lose a variable number of mannose residues and acquire a more complex structure during a process called 'terminal glycosylation'. This process yields 3 types of mature N-glycans: high mannose (those that have escaped terminal glycosylation), hybrid and complex (with different combinations of mannose, N-acetylglucosamine, N-acetylgalactosamine, fucose and sialic acid residues).

O-linked glycosylation refers to the attachment of glycans to the oxygen atom in the side chain of Serine and Threonine residues. This modification occurs in secreted and membrane proteins of eukaryotes, and resulting O-linked glycans play important roles in protein localization and trafficking, protein solubility, antigenicity and cell-cell interactions. The process is a post-translational event that takes place in the cis-Golgi compartment after N-glycosylation and folding of the protein. O-linked glycans are built in a stepwise fashion with sugars being added incrementally. The most common type of O-glycosylation in secreted and membrane-bound mammalian proteins is the addition of reducing terminal N-acetylgalactosamine (GalNAc) to yield "mucin-type" O-linked glycans. This residue can be further extended with galactose (Gal), N-acetylglucosamine (GlcNAc) or GlcNAc and Gal resulting in 8 common core structures, which are often further decorated with the addition of up to three sialic acid residues. In addition to the "mucin-type" glycans, a variety of mammalian proteins are known to have mannose (Man), fucose (Fuc), glucose (Glc), galactose (Gal) or xylose (Xyl) as reducing terminal linkages.

Some eukaryotic cytoplasmic and nuclear proteins have simple O-linked glycans in which a single N-acetylglucosamine is linked to a serine or a threonine residue. This type of glycosylation plays an important role in the modulation of the biological activity of intracellular proteins, and in some proteins the same residue may be subject to competing phosphorylation and O-linked glycosylation.

C-linked glycosylation refers to covalent attachment of mannose residue to Tryptophan residues within an extracellular protein. Two recognition signals for C-mannosylation have been proposed: W-X-X-W (in which the first or both tryptophan residues become mannosylated), and W-S/T-X-C.

Glycation refers to the non-enzymatic attachment of reducing sugars to Nitrogen atoms of proteins (N-termini and Lysine and Histidine side chains) in a process known as the "Maillard" reaction. Sugars bound to glycated proteins are gradually modified to become Advanced Glycation End products (AGEs), which have been implicated in a variety of diseases including type II diabetes mellitus, cancer, atherosclerosis, Alzheimer's disease and Parkinson's disease.

Protein glycosylation has been linked with a variety of human diseases. For example aberrant protein glycosylation is an established event in cancer development and progression (Hakomori S (1989), *Advances in Cancer Research* 52:257-331; Hakomori S I and Cummings R D (2012), *Glycoconjugate Journal* 29(8-9):565-566). Additionally, defects in protein glycosylation have been implicated in a number of cellular storage disorders including Gaucher's, Niemann-Pick type C, Sandhoff's, and Tay-Sachs diseases (Ohtsubo K and Marth J D (2007), *Cell* 126:855-867), and more recently protein glycosylation has been linked to the onset of cardiovascular disease (Akinkoulie A O et al (2014), *Journal of the American Heart Association* 3(5):e001221). Credible hypotheses supporting a role for protein glycosylation in the pathology and epidemiology of Alzheimer's disease have also been proposed recently (Schedin-Weiss S et al (2014), *FEBS Journal* 281:46-62).

Sugars covalently attached to proteins are identifiable using lectins, proteins that recognise and bind to specific glycans. Lectins were initially discovered in plants and are now known to be ubiquitous in nature. Each lectin has distinct glycan specificity, and generation of a glycosylation profile for any given protein therefore requires testing against a multitude of individual lectins. Existing technologies for generation of protein glycosylation profiles using this approach requires the use of one or more reporter tags or indirect methods to allow detection of and to distinguish binding of individual lectins and/or antibodies to glycoproteins immobilised on or bound to a surface (see e.g. Chen S et al (2007) *Nature Methods* 4(5):437-444; and Meany D L et al (2009) *Journal of Proteome Research* 8(2):613-619). Alternatively, if a small number of reporter tags are available, generation of protein glycosylation profiles is a substantial task that requires that the glycoproteins immobilised on or bound to a surface are serially exposed to a small number of lectins so as to build up the number of data points required to produce that profile (Goodarzi M T and Turner G A (1997), *Glycoconjugate Journal* 14(4):493-496). However, mass spectrophotometric methods remain the gold standard for comprehensive one step analysis of protein glycosylation (Wada Y et al (2007), *Glycobiology* 17(4):411-422).

It has been reported that protein glycosylation may interfere with or indeed prevent binding of a protein by an antibody that specifically recognises the protein in a non-glycosylated state (De Groot A S and Scott D W (2007), *Trends Immunol* 28: 482-490). This can lead to underestimates of protein levels in samples and to false results in diagnostic tests.

There is a need for improved methods for the detection and measurement of glycosylated proteins, for the generation of glycosylation profiles for such proteins and for the use of protein glycosylation in the screening, diagnosis, prognostication and treatment of human disease.

SUMMARY OF THE INVENTION

The present invention is based on the discovery that contacting a target biological molecule, preferably protein with an antibody that recognises specifically that target and a specific lectin (or other glycan-binding agent) that recognises a sugar on that target, on a reaction substrate allows for the determination of a glycosylation profile for the target in a single step. In one embodiment, the lectin and antibody-binding reactions on a single discrete test region on the same substrate or on discrete test areas allows for the determination of a glycosylation profile to be carried out effectively in an essentially single process.

Thus, in a first aspect, there is a method of determining the glycosylation signature of a target biological molecule in a sample obtained from a patient comprising the steps of: (a) contacting the sample with a substrate-immobilised capture antibody that binds specifically to the target; (b) contacting the target bound to the immobilised capture antibody with a detection antibody that specifically binds the target; (c) contacting the target bound to the immobilised capture antibody with one or more distinct glycan-binding agents, each having a distinct (i.e. different) glycan specificity; (d) measuring the level of the target bound by the detection antibody in (b); and (e) measuring the level of agents bound to the target in (c).

The method may be carried out to determine the presence on the target of a single glycan type, or, preferably a plurality of different glycans present, or potentially present, on the target.

In a second aspect, there is a method of determining the level of a target biological molecule in a sample obtained from a patient comprising the steps of: (a) contacting the sample with a substrate immobilised capture antibody that binds specifically to the target; (b) contacting the target bound to the immobilised capture antibody with a detection antibody that specifically binds the target; (c) contacting the target bound to the immobilised capture antibody with a glycan-binding agent; (d) measuring the level of the target bound by the detection antibody in (b); and (e) measuring the level of the target bound by the glycan binding agent in (c).

Again, the method may be carried out to determine the presence of a single glycan type, or may be carried out to determine the presence of a plurality of different glycans.

DESCRIPTION OF THE FIGURES

FIGS. 1 and 2 show schematic representations for a 2 to 9 biochip assay measuring protein levels, protein binding of up to 6 lectins, protein autoantibody levels and anti-glycan autoantibody levels.

FIGS. 3 and 4 show schematic representations for a 4 biochip assay measuring protein levels, protein binding of more than one lectin, protein autoantibody levels and anti-glycan autoantibody levels.

FIGS. 5 to 7 show schematic representations for a single biochip assay.

FIGS. 8 and 9 show schematic representations of a 3 to 9 biochip assay incorporating measurement of deglycosylation reaction.

DETAILED DESCRIPTION OF THE INVENTION

Figure 1:
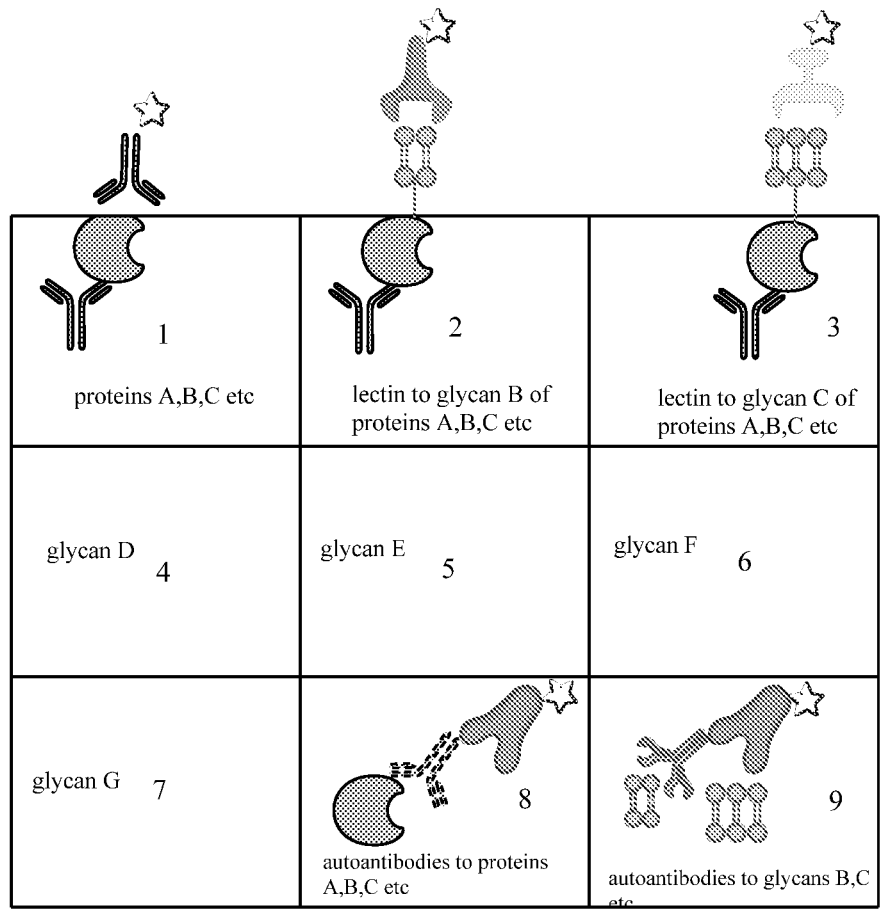

The present invention is based on an appreciation that contacting a target biological molecule, preferably a protein, with an antibody that specifically recognises that target and one or more glycan-binding agent(s) that recognises a sugar on that target, in discrete areas on a reaction substrate allows for the determination of a glycosylation signature or profile for the target. The reactions for determining the presence of different glycans may be carried out on the same discrete test region (DTR) when using detection molecules that can discriminate between the reactions i.e. to discriminate between the detection of different glycans, or when interrogating different targets, each target immobilised at the discrete test region of the substrate. Alternatively, if the same detection molecule is to be used for reactions involving different species i.e proteins, peptides or carbohydrate antigens and glycans etc, physical separation of the different reaction sites is preferably required for each target so that the user can discriminate between which target is being characterised. For example, when the same detection molecule is to be used, the reactions for determining different glycans present on the same target species may be carried out on physically separate reaction substrates, e.g. biochips or on a single substrate which incorporates Discrete Test Areas, such as a microtitre plate. The present invention provides for efficient and cost-effective generation of a glycosylation profile for a target molecule from a sample obtained from a patient. This is a significant breakthrough in the characterisation of protein glycosylation in patient samples.

The following definitions apply to terms used throughout this description and in relation to any of the aspects of the invention described herein.

The terms "patient" and "subject" are used interchangeably herein and refer to any animal (e.g. mammal), including, but not limited to, humans, non-human primates, canines, felines, rodents and the like, which is to be the recipient of the diagnosis. Preferably, the subject or patient is a human.

The term "target biological molecule" refers to any biological molecule which may be subject to glycosylation. This includes proteins, peptides, glycan or glycosaminoglycan-containing molecules or microbial analytes and carbohydrate antigens The "level" of a protein refers to the amount, expression level or concentration of the protein within the sample. The "level" of antibodies or autoantibodies refers to the amount, expression level or concentration of antibodies or autoantibodies within the sample. The level of a protein, the level of antibodies or the level of autoantibodies may also refer to the protein, antibodies or autoantibodies measurement expressed as a ratio or percentage of the level of one or more other analytes. The level of one or more such other analytes may remain consistent in the majority of samples or conditions. For example, the ratio of total protein to glycosylated protein may be calculated. The term "analyte" refers to the species being detected and measured.

The level of a protein may also refer to the protein measurement expressed as a ratio or percentage of the level of one or more other analytes, where the level of the one or more other analytes is proposed to hold some biochemical significance to the clinical condition of interest. The level of antibodies or autoantibodies may also refer to the antibodies or autoantibodies measurement expressed as a ratio or percentage of the level of one or more other analytes, where the level of the one or more other analytes is proposed to hold some biochemical significance to the clinical condition of interest.

As used herein, the term "a sample" includes biological samples obtained from a patient or subject, which may comprise blood, plasma, serum, urine, saliva or sputum.

The term "cancer" refers to or describes the physiological condition in mammals in which a population of cells are characterised by unregulated cell growth.

The terms "cancer cell" and "tumour cell" are grammatical equivalents referring to the total population of cells derived from a tumour or a pre-cancerous lesion. The terms "tumour" and "neoplasm" are used interchangeably herein and refer to any mass of tissue that results from excessive cell growth, proliferation and/or survival, either benign (noncancerous) or malignant (cancerous), including pre-cancerous lesions.

The methods of the invention described herein are carried out ex vivo. For the avoidance of doubt, the term "ex vivo" has its usual meaning in the art, referring to methods that are carried out in or on a sample obtained from a subject in an artificial environment outside the body of the subject from whom the sample has been obtained.

The term "metastasis" and related terms "metastases" and "metastatic" refers to a cancer or tumour that has spread from the original site in which it developed and has invaded and/or is growing in other tissues, forming new tumour growths and obstructions.

The terms "immunoassay", "immuno-detection" and "immunological assay" are used interchangeably herein and refer to antibody-based techniques for identifying the presence of or levels of a target molecule (e.g. protein) in a sample. Examples of such assays and methods are well known to those of skill in the art.

The term "glycosylation profile" or "glycosylation signature" of a target or a defined group of targets refers to the type of glycans attached to one or more targets; the profile can be expressed qualitatively in terms of which glycan-binding agents it binds or quantitatively in terms of the amount of a particular glycan-binding agent it binds, for example as a concentration or a ratio. For example, the glycosylated protein level may be expressed as a ratio of total protein level to glycosylated protein level. The terms "profile" and "signature" are used interchangeably.

The term "reporter molecule" refers to a label that is covalently attached to the antibody or glycan-binding agent to enable its detection, and such reporters include but are not limited to radionuclides, fluorophores, dyes or enzymes including, for example, horse-radish peroxidase and alkaline phosphatase.

The term "probe" refers to a molecule that is capable of specifically binding to a target molecule such that the target molecule can be detected as a consequence of said specific binding. Probes may be immobilised on a surface to capture the target molecule they specifically bind, or probes may be exposed to an immobilised protein, antibody or autoantibody to detect molecules they specifically bind. Probes that can be used in the present invention include, for example, antibodies, glycan-binding agents, molecular imprinted polymers, aptamers and oligonucleotides.

The term "antibody" refers to an immunoglobulin which specifically recognises an epitope on a target as determined by the binding characteristics of the immunoglobulin variable domains of the heavy and light chains ($V_H$s and $V_L$s), more specifically the complementarity-determining regions (CDRs). Many potential antibody forms are known in the art, which may include, but are not limited to, a plurality of intact monoclonal antibodies or polyclonal mixtures comprising intact monoclonal antibodies, antibody fragments (for example $F_{ab}$, $F_{ab}'$, and $F_v$ fragments, linear antibodies single chain antibodies and multi-specific antibodies comprising antibody fragments), single-chain variable fragments ($scF_v$s), multi-specific antibodies, chimeric antibodies, humanised antibodies and fusion proteins comprising the domains necessary for the recognition of a given epitope on a target. Preferably, references to antibodies in the context of the present invention refer to monoclonal antibodies. Antibodies may also be conjugated to various detectable labels to enable detection, including but not limited to radionuclides, fluorophores, dyes or enzymes including, for example, horse-radish peroxidase and alkaline phosphatase.

The term "autoantibody" refers to an antibody that is present in a sample obtained from a patient and that is directed against one or more of the patient's own proteins or against a post-translational modification of one or more of the patient's own proteins. Such post-translational modifications recognised by autoantibodies in a sample obtained from a patient include glycosylation. Many autoimmune diseases, (notably lupus erythematosus), are caused by such autoantibodies.

The term "capture antibody" refers to an antibody that is immobilised on the surface of a substrate, it recognises specifically a target in a sample and it binds specifically to and immobilises that target to the surface of the substrate. The capture antibody can be selected to recognise specifically an epitope of a target e.g. protein which has no consensus glycosylation sites or an epitope which is sufficiently distant from a consensus glycosylation site to ensure that glycosylation on the target does not affect specific binding by the antibody. This ensures efficient binding by the capture antibody of unglycosylated target and can also prevent possible interference during binding of glycan to glycan-binding agent.

The term "detection antibody" refers to an antibody that recognises specifically a target. It is preferably covalently attached to a reporter molecule. It binds specifically to the target that is bound and immobilised by the capture antibody, and this binding is detected by the presence of a reporter molecule (which is usually covalently attached thereto). The detection antibody can be selected to recognise specifically an epitope of a target protein which has no consensus glycosylation sites or an epitope which is sufficiently distant from a consensus glycosylation site to ensure that target protein glycosylation does not affect specific binding by the antibody. This ensures efficient binding by the detection antibody of unglycosylated target proteins and can also prevent possible interference during binding between the glycan and glycan-binding agent.

The term "aptamer" refers to an oligonucleotide molecule or a polypeptide molecule that binds specifically to a target molecule. Oligonucleotide aptamers may be ribonucleotides (RNA) or deoxyribonucleotides (DNA) and typically consist of short strands of oligonucleotides. Polypeptide aptamers typically consist of short peptide domains that may be attached at one end or at both ends to a protein scaffold.

The term "glycan" refers to sugar moieties that are found attached to proteins as in glycoproteins and proteoglycans. While typically consisting of a large number of monosaccharides linked glycosidically, "glycans" include the carbohydrate portion of any glycoconjugate, such as a glycoprotein, glycolipid, or a proteoglycan, even if the carbohydrate is only an oligosaccharide.

The term "glycan-binding agent" refers to an agent that binds specifically to a glycan. Glycan binding agents can include, but are not limited to lectins isolated from plant sources, recombinant lectin molecules identified from microbes or antibodies raised against glycan immunogen targets including monoclonal antibodies, derivative recombinant antibody fragments including antigen binding (Fab) fragments, single chain variable fragments (scFvs), single chain antibodies. Purified or recombinant glycan or glycosaminoglycan binding proteins and peptides may also be employed in glycan-specific detection including R-type, C-type, P-type, C-type and I-type lectins, galectins from mammalian, microbial or plant sources, aptamers and molecular imprinted polymers. Preferably, the glycan-binding agent is a lectin.

The term "epitope" refers to the portion of a target which is specifically recognised by a given antibody. In instances where the antigen is a protein, the epitope may be formed from either a contiguous or non-contiguous number of amino acids ('linear' or 'conformation' epitopes respectively), whereby in the case of the latter, residues comprising the epitope are brought together in the three-dimensional fold of the polypeptide. An epitope typically comprises, but is not limited to, 3-10 amino acids in specific positions and orientations with respect to one another. Techniques known in the art for determining the epitope recognised by an antibody (specifically whether or not an epitope comprises a given residue) include but are not limited to, site-directed mutagenesis or the use of suitable homologous proteins to the target biological molecule, e.g. protein, in combination with techniques for determining specific recognition or lack thereof, as exemplified below. By way of example and not limitation, an epitope may be determined as comprising a given residue by comparative analysis with a control comprising specific recognition of the native (non-substituted) target protein by said antibody; wherein diminished binding and/or lack of specific recognition by said antibody when compared with said control identifies a given residue as forming part of an epitope. Furthermore, structural analyses of antibody-target protein complexes via x-ray crystallography and/or nuclear magnetic resonance (NMR) spectroscopy, or suitable derivatives thereof, may also be used to determine the residues which constitute an epitope.

The term "binds specifically", in the context of antibody-epitope interactions, refers to an interaction wherein the antibody and epitope associate more frequently or rapidly, or with greater duration or affinity, or with any combination of the above, than when either antibody or epitope is substituted for an alternative substance, for example an unrelated protein. Generally, but not necessarily, reference to binding means specific recognition. Furthermore, it is appreciated that an antibody may recognise more than one antigen specifically, for example, an antibody that binds specifically to a protein in its unglycosylated form may also bind specifically to it in a glycosylated form. Additionally, an antibody that binds specifically to a protein in its unglycosylated form may be unable to bind specifically to it in a glycosylated form. Techniques known in the art for determining the specific binding of a target by a monoclonal antibody or lack thereof include but are not limited to, FACS analysis, immunocytochemical staining, immunohistochemistry, western blotting/dot blotting, ELISA, affinity chromatography. By way of example and not limitation, specific binding, or lack thereof, may be determined by comparative analysis with a control comprising the use of an antibody which is known in the art to specifically recognise said target and/or a control comprising the absence of, or minimal, specific recognition of said target (for example wherein the control comprises the use of a non-specific antibody). Said comparative analysis may be either qualitative or quantitative. It is understood, however, that an antibody or binding moiety which demonstrates exclusive specific recognition of a given target is said to have higher specificity for said target when compared with an antibody which, for example, specifically recognises both the target and a homologous protein.

A protein present in a sample isolated from a patient having a disease may have levels which are different to that of a control. However, the levels of some proteins that are different compared to a control may not show a strong enough correlation with disease such that they may be used to diagnose disease with an acceptable accuracy. Accuracy of a diagnostic method is often described by its receiver-operating characteristics (ROC) (Zweig, M. H., and Campbell, G., Clin. Chem. 39 (1993) 561-577). The ROC graph is a plot of all of the sensitivity/specificity pairs resulting from continuously varying the decision threshold over the entire range of data observed.

A ROC plot depicts the overlap between the two distributions by plotting the sensitivity versus 1—specificity for the complete range of decision thresholds. On the y-axis is sensitivity, or the true-positive fraction defined as [(number of true-positive test results)/(number of true-positive+number of false-negative test results)]. This has also been referred to as positivity in the presence of a disease or condition. It is calculated solely from the affected subgroup. On the x-axis is the false-positive fraction, or 1—specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. Qualitatively, the closer the plot is to the upper left corner, the higher the overall accuracy of the test.

One convenient goal to quantify the diagnostic accuracy of a laboratory test is to express its performance by a single number. The most common global measure is the area under the curve (AUC) of the ROC plot. The area under the ROC curve is a measure of the probability that the perceived measurement will allow correct identification of a condition. By convention, this area is always 0.5. Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0). In the context of the present invention, the two different conditions are whether a patient has or does not have cancer or alternatively whether a patient who has cancer has only a primary tumour or has metastatic disease. The ROC plot data and the clinical requirements of the test may be considered together when calculating a threshold or "cut-off" value to be used in future application of the diagnostic test. When the analyte value is measured above (or below) this cut-off value, the test is considered "positive" and further action may be taken appropriate to the clinical condition. An important feature in setting the cut-off value is the required specificity of the test (i.e. the true negative rate). By convention, the required specificity for many diagnostic tests is stated in advance to be 90%, 95%, or as close to 100% as practical. For cancer biomarker tests, it is likely that an effective test will need to approach 100% due to the relatively low prevalence of cancer in the general population (or even targeted populations) compared to those with inflammatory diseases and also on account of the severe consequences of false negative results for patients. The analyte cut-off value required to achieve these specificities may then be read from the ROC plot. This point on the plot will also denote a value for test sensitivity (true positive rate). Alternatively, the optimum cut-off value may be obtained by selecting the point on the ROC curve closest to the top-left corner of the graph. In the present invention, in a preferred embodiment, the AUC measurements can be improved by calculating ratios based on total protein levels of a biomarker protein and glycosylated protein levels of the same biomarker protein. In further embodiments the AUC measurements can be improved by calculating ratios based on measurements derived from intra and inter species comparison of one or more of the following species: total protein levels, unglycosylated protein levels, glycosylated protein levels, levels of autoantibodies to proteins, levels of autoantibodies to glycans and levels of individual glycans e.g. level of total protein A vs level of glycosylated protein A, level of total protein A vs level of unglycosylated protein A, level of unglycosylated protein A vs level of autoantibodies to protein A etc. Additionally or alternatively comparisons can be made or ratios calculated between these levels in different analytes e.g protein A and protein B.

Proteins that will be immobilised may be purified variants of the target protein. Protein targets may be produced using gene transfer into bacterial expression systems including *E coli, Corynebacterium* sp and *Pseudomonas fluorescens*; eukaryotic expression systems including yeast e.g. *Saccharomyces cerevisiae*, Pichia Pastoris, Filamentous fungi, including *Aspergillus* sp, *Trichoderma*, and *Myceliophthora thermophila* C1, insect-derived cell lines including Sf9, Sf21 from *Spodoptera frugiperda* cells, Hi-5 from *Trichoplusia ni* cells, and Schneider 2 cells and Schneider 3 cells from *Drosophila melanogaster* cells and mammalian-derived expression systems in cell lines including Chinese Hamster Ovary, Human Embryonic Kidney cells. Proteins may also be produced synthetically using methods including cell-free synthesis or organic chemistry-based methods to produce full length or specific protein fragments. Targets can also include derivative synthetic peptides, glycopeptides or other protein fragments containing relevant target epitopes. The proteins may also be purified from human samples, e.g. human tissue or human plasma. Alternatives will be apparent to the skilled person.

An effective diagnostic biomarker (target protein) test will need to approach 100% specificity. Diagnostic tests that are 100% specific and 100% sensitive, i.e., that produce no false positive or false negative results, are considered ideal. However, a low level of false results can be acceptable, and so biomarkers demonstrating specificity close to 95% or above often acceptable.

The present invention may be used to determine the glycosylation signature of one or more target molecules in a patient sample. The purpose may be to determine aberrant levels of glycosylation on a specific target which may be indicative of a disease state. Defects in glycosylation may also be determined, again providing an indicative of a potential or actual disorder. The present invention may also be used to improve diagnostic assays, where conventional analysis of biomarkers is hindered by under detection of a biomarker due to the interfering presence of glycosylation. The present invention allows determination of the extent of glycosylation to be made, which allows a recalibration to be made of the biomarker result.

The present invention has identified that contacting a target biological molecule, e.g. protein, with an antibody that specifically recognises that target and a specific glycan-binding agent that recognises a sugar on that target, on the same DTR of a reaction substrate, allows for the determination of a glycosylation profile for the target (e.g. see FIG. 5).

In one embodiment, different detector molecules are used to identify binding of each different glycan-binding agent and/or the antibody binding to the target molecule. The reactions are therefore discriminated on the basis of the signal produced. In an alternative embodiment, the DTA contains a plurality of reaction sites, each intended as a site for immobilising different target molecules. In this embodiment, it is possible to use the same detection molecule, as discrimination is due to knowledge as to which target molecule is localised at which site on the DTA. It will be evident that the reactions can be carried out in parallel or at substantially the same time, i.e. in the same process, depending on the design of the experiment.

Additionally, the present invention has identified that physical separation of the glycan-binding agent and antibody binding reactions on the substrate or on separate substrates allows this process for the determination of a glycosylation signature to be carried out effectively using the same detection molecule on the antibody and the glycan-binding agent (e.g FIGS. 1 & 2). This provides for efficient and cost-effective generation of a target glycosylation profile from a single sample obtained from a patient. This is a significant breakthrough in the characterisation of glycosylation signatures in patient samples e.g. protein glycosylation signatures, and provides for improved patient diagnosis and treatment as it allows glycosylation profiles to be efficiently and cost-effectively developed for samples obtained from patients at risk of or suspected of suffering disease. In this context, when using the same detection molecule to identify binding for different glycan-binding agents, it will be understood that physical separation of the reactions will be necessary so that the detected signal can be properly associated with the correct glycan under study. It is possible that multiple different targets can be detected using the same detection molecule at spatially separate discrete test regions on the same substrate. For example, multiple target proteins (proteins A, B, C, etc.) can be detected on chip 1 of FIG. 1. The spatial separation allows the discrimination of the results for the detection signal.

A first aspect of the present invention provides a method of determining the glycosylation signature of a target biological molecule in a sample obtained from a patient comprising the steps of: (a) contacting the sample with a substrate-immobilised capture antibody that binds specifically to the target; (b) contacting the target bound to the immobilised capture antibody with a detection antibody that specifically binds the target; (c) contacting the target bound to the immobilised capture antibody with one or more distinct glycan-binding agents, each having a different glycan specificity; (d) measuring the level of target bound by detection antibody in (b); and (e) measuring the level of agents bound to the target in (c).

In specific embodiments, steps (b) and (c) are carried out at the same time. In the present invention, the carrying out of reaction steps "at the same time" can mean that the reactions are carried out simultaneously, where more than one reaction is performed on the same DTR (different detection molecules need to be utilised) or in parallel where the reactions are physically separated and one reaction is performed per DTR (same detection molecule can be utilised).

In further specific embodiments the antibody that specifically binds the target in (b) and one or more of the plurality of glycan-binding agents in (c) are detected using the same type of reporter molecule and wherein the reactions (b) and (c) are carried out in physically separated reactions sites. As the reporter molecule (i.e. that molecule which results in a detectable signal) is the same for different reactions, it is necessary to separate the reactions, so that the detectable signal can be categorised appropriately.

In further specific embodiments the method includes additional steps of (f) contacting the sample with a capture protein immobilised on the substrate, said capture protein being of the same type as the target; and (g) measuring the level of antibodies (autoantibodies) in the sample that bind to the capture protein. By "same type", it is understood that purified or synthetic or recombinant versions of the target may be used. In this embodiment, it is intended that there be a separate reaction that monitors the level of autoantibodies targeting the target molecule present in the patient sample. The autoantibodies may be specific to one or more of the targets being screened. This information, as well as being used diagnostically, may also be used to gauge the extent to which the assay on step (a) or (b) may be compromised due to autoantibodies binding to the target(s) under study.

The determination of autoantibody levels may be carried out on a physically separate substrate from that of the other reactions. Autoantibodies to one or more of the targets may be determined on a single substrate with separate discrete test regions (DTRs) or on separate substrates.

In further specific embodiments steps (a) and (f) are each carried out in physically separated sites, with the steps performed at substantially the same time, and in further specific embodiments steps (b) and (c) are carried out at the same time.

In further specific embodiments the method further comprising the steps of (h) contacting the sample with a capture glycan immobilised on the substrate and (i) measuring the level of antibodies (autoantibodies) in the sample that bind to the capture glycan. In this embodiment it is intended that there be a specific reaction that monitors the level of autoantibodies specific for glycosylated molecules present, in the sample. The autoantibodies may be specific to one or more glycans present on the target(s) under study. The information gained from this, as well as being used diagnostically, may be used to give an indication that the assay in step (c) may be compromised due to autoantibodies binding to the glycans.

The determination of autoantibody levels will preferably be carried out on a physically separate discrete test area from that of the other reactions.

In specific embodiments steps (a) and (h) (and optionally (f)) are carried out at the same time, i.e. in parallel, while in further specific embodiments steps (b), (c) and (i) (and optionally also (g)) are carried out in the same process, i.e. are carried out in parallel.

In particular embodiments the method steps are carried out on a multiplexed array. This is demonstrated in the figures, where FIG. 1 shows a multiplexed array with separate targets being characterised (glycosylation signature characterised) on separate (distinct) reaction substrates (herein also referred to as Discrete Test Areas (DTAs)). Physical separation of the different reactions can be used, or in certain circumstances, as shown in the accompanying figures, many of the reactions can occur on the same substrate (DTA) at the same Discrete Test Region for each separate target, where discrimination of the results is permissible e.g. FIGS. 5 and 6.

A second aspect of the present invention provides a method of determining the level of a target biological molecule in a sample obtained from a patient comprising the steps of: (a) contacting the sample with an immobilised capture antibody that binds specifically to the target; (b) contacting the target bound to the immobilised capture antibody with a detection antibody that specifically binds the target; (c) contacting the target bound to the immobilised capture antibody with a glycan-binding agent; (d) measuring the level of the target bound by detection antibody in (b); and (e) measuring the level of the target bound by the glycan-binding agent in (c).

A third aspect of the present invention provides a substrate comprising an assay chip on which is immobilised a capture antibody that specifically binds to a target biological molecule and a further assay chip on which is immobilised a protein that is specifically bound by that capture antibody or an alternative capture antibody which binds to a different epitope of the target protein.

In particular embodiments the substrate comprises an assay chip on which is immobilised a glycan that is specifically recognised by a glycan autoantibody in a sample obtained from a patient.

In particular embodiments the substrate is used in a method of the invention.

A fourth aspect of the present invention provides a method of identifying the presence or absence of a disease in a patient comprising at least one of the steps of: (a) determining the glycosylation signature of the target in the sample obtained from a patient by carrying out the method of the first aspect above; (b) determining the level of the target in the sample obtained from a patient by the method of the second aspect above; (c) measuring the level of autoantibodies to the target in the sample; (d) determining the glycan autoantibody signature in the sample; and (e) compiling a patient profile based on the results obtained from any one or more of steps (a)-(d), wherein the patient profile of (e) indicates the presence or absence of the disease.

In particular embodiments the level of the target (step (b)) is determined by measurement of binding by a specific detection antibody, wherein the glycan signature of that target is determined by measurement of binding by a specific glycan-binding agent, wherein the level of autoantibodies to that target is determined by measurement of specific autoantibody binding to the target and wherein the glycan autoantibody profile is determined by measuring specific autoantibody binding to the target glycan.

In further particular embodiments the steps are carried out on a multiplexed array, where two or more targets are to be interrogated at the same or similar time. Accordingly, a single discrete test area may be used to carry out multiple reactions.

In preferred embodiments of any of the aspects of the invention, the target in a sample obtained from a patient is selected from the group consisting of monoamine oxidase B (MAO-B), tropomyosin, coagulation factor XIII, Apolipoprotein E (APOE), Glutathione S-transferase Omega-1 (GSTO-1), P-Selectin, L-selectin, E-selectin, Monocyte chemotactic protein 1 (MCP-1), Interleukin-1α (IL-1α), Interleukin-1β (IL-1β), Interleukin-8 (IL-8), Interferon-α (INF-α), Vascular Endothelial growth factor (VEGF), Endothelial growth factor (EGF), afamin, alpha-1-antichymotrypsin, alpha-2-macroglobulin, Apolipoprotein B100 (APOB100), complement C3, complement C5, TANK binding kinase 1 (TBK-1), vitamin D binding protein, alpha-1-B glycoprotein, hemopexin, serum albumin, ceruloplasmin, alpha 2 antiplasmin, apolipoprotein A1, complement factor H, Immunoglobulin G (IgG), Immunoglobulin G Fc binding protein, hornerin, fibrinogen, Carcinoembryonic antigen (CEA), Neutrophil gelatinase-associated lipocalin (NGAL), Neuron specific enolase (NSE), Interleukin-2 (IL-2), Thrombomodulin (TM), D-dimer, Matrix Metallopeptidase 9 (MMP9), MMP9/NGAL complex, Fas ligand, C-reactive protein (CRP), Nuclear Matrix Protein 22 (NMP22), Bladder Tumour Antigen (BTA), Cytokeratin 18 (CK-18), Interleukin-1 (IL-1), Tumour Necrosis Factor α (TNF α), Soluble tumour necrosis factor receptor 1 (sTNFr1), Soluble tumour necrosis factor receptor 2 (sTNFr1), Free Prostate-Specific Antigen (FPSA), Total Prostate-Specific Antigen (TPSA), Hyalurinidase (HA), Interleukin-10 (IL-10), von Willebrand Factor (vWF), Factor VII, Nicotinamide Phosphoribosyltransferase (NAMPT), Intercellular adhesion molecule 1 (ICAM-1), Vascular Cell Adhesion Molecule 1 (VCAM-1), Fatty acid-binding protein 1 (FABP1), Fatty acid-binding protein 2 (FABP2), Fatty acid-binding protein 3 (FABP3), Fatty acid-binding protein 4 (FABP4), Fatty acid-binding protein 5 (FABP5), Fatty acid-binding protein 6 (FABP6), Fatty acid-binding protein 7 (FABP7), Fatty acid-binding protein 8 (FABP8), Fatty acid-binding protein 9 (FABP9), Glial Fibrillary Acidic Protein (GFAP), S100 calcium binding protein A10 (S100A10), S100 calcium binding protein A11 (S100A11), Interleukin-18 (IL-18), Interleukin-1 receptor antagonist (IL1-ra), α-Glutamyl transpeptidase (α-GT), Aspartate transaminase (AST), Cystatin C (CysC), C3aDesArg, troponin T (TnT), troponin I (TnI), Macrophage Inflammatory Protein 1α (MIP-1α), Adiponectin, Cluster of Differentiation 26 (CD26), GMCSF, Interleukin-15 (IL-15), Interleukin-5 (IL-5), soluble interleukin 2α (sIL-2α, soluble interleukin 6 receptor (sIL-6r), pyruvate kinase isozyme type M2 (M2-PK), secretory leukocyte proteinase inhibitor (SLPI), Carbohydrate antigen 125 (CA-125), Carbohydrate antigen 19-9 (CA-19-9), Prostate-specific antigen (PSA), BRCA1, BRCA2, Cluster of Differentiation 15 (CD15), Cluster of Differentiation 20 (CD20), Cluster of Differentiation 30 (CD30), Cluster of Differentiation 45 (CD45), Human epidermal growth factor receptor 2 (HER-2), brain natriuretic peptide (Pro-BNP), glycogen phosphorylase BB (GPBB), myoglobin, aspartate transaminase (AST), lactate dehydrogenase (LDH), creatine kinase (CK). It will also be understood that variants, fragments or domains of these proteins would also be suitable targets.

In preferred embodiments of any of the aspects of the invention, the specific glycan-binding agent is a lectin, e.g Dolichos Biflorus Agglutinin (DBA), Concanavalin A (ConA) Con A, Bauhinia purpurea lectin (BPA), Peanut agglutinin (PNA), Glycine max (soybean) (SBA), Ulex europaeus agglutinin (UEA), Griffonia simplicifolia 1 isolectin B4 (GS1 B4), Griffonia simplicifolia 11 (Gs-11), Wheat germ agglutinin (WGA), Maclura pomifera Lectin (Osage Orange) (MPA), Sambucus nigra (Elderberry) lectin (SNA I), Pisum sativum lectin (PSA), Succinylated Wheat germ agglutinin (Suc-WGA), phytohaemagglutinin (PHA-L), Lens culiinaris agglutinin (LCA), Phaseolus vulgaris lectin E (PHA-E), Sophora japonica agglutinin (SJA), Ricinus communis Agglutinin, RCA), Aleuria Aurantia Lectin (AAL), Recombinant lectins derived from plant or microbial sources.

In further preferred embodiments, the disease is selected from the groups consisting of cardiovascular disease, a neurological disorder e.g. Alzheimer's disease, cancer, an inflammatory disorder or metabolic syndrome. In the most preferred embodiment, the disease is a cancer, e.g. pancreatic cancer.

The sample may be a urine sample, blood sample, serum sample, plasma sample, saliva sample or sputum sample.

Figure 6:
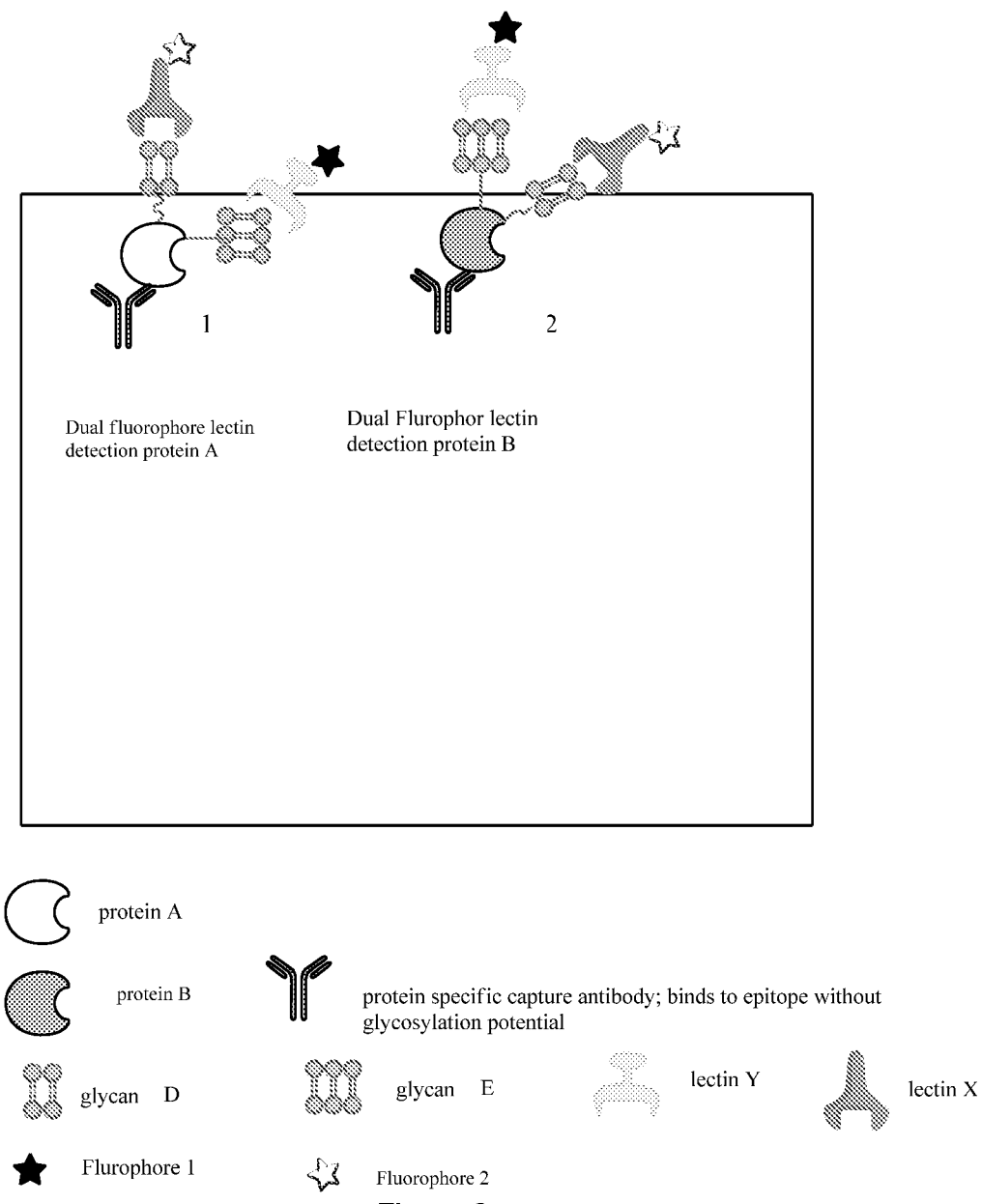
Figure 7:
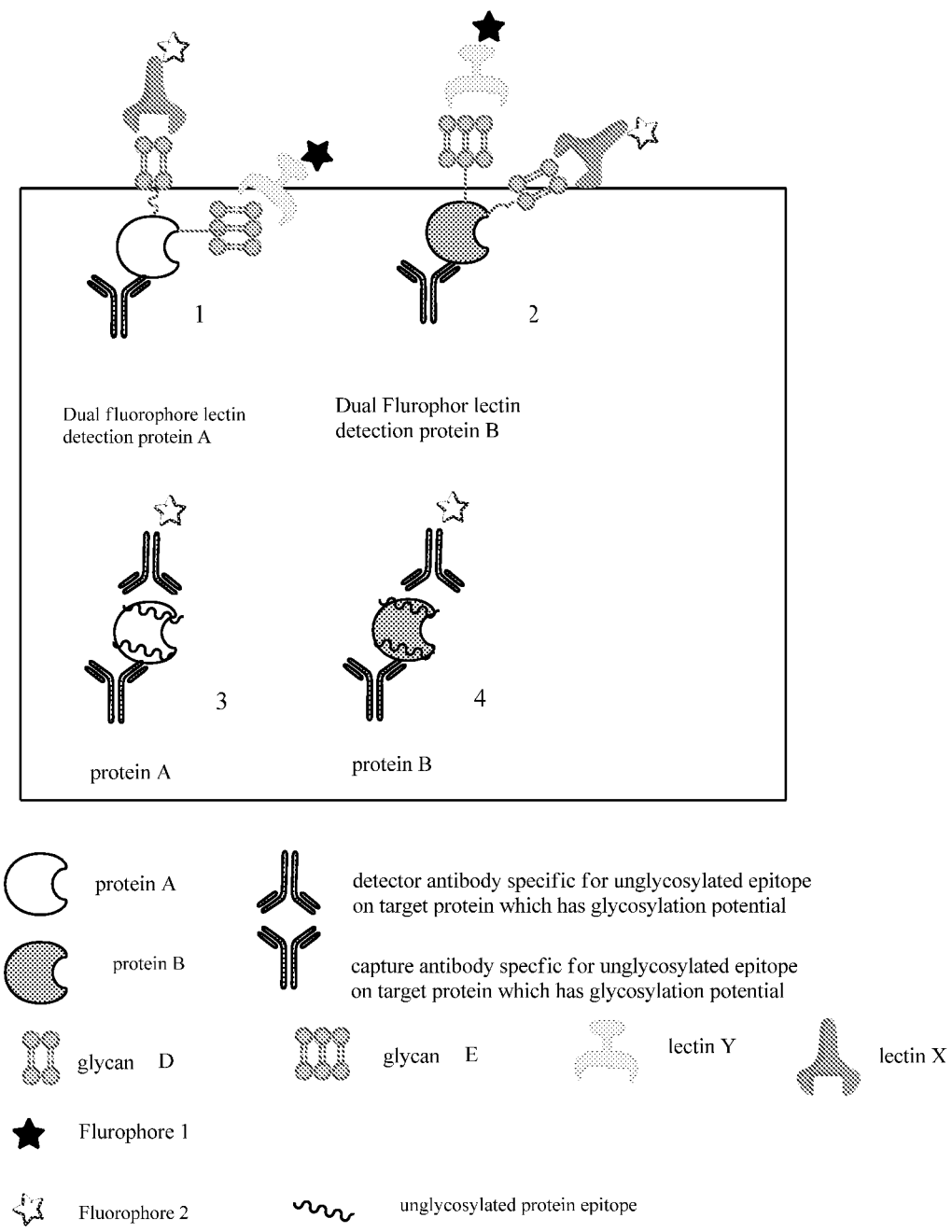

The determination of the level of a target, e.g. protein, antibodies or autoantibodies in the sample may be determined by immunological methods such as an ELISA-based assay. Preferably, the methods of the present invention use a solid-state device for determining the level of a protein, antibodies or autoantibodies in the sample isolated from the patient. The solid-state device comprises a substrate on which is immobilised a probe that binds specifically to a target, e.g. protein, antibodies or autoantibodies. Such probes may be immobilised at discrete areas of an activated surface of the substrate. The solid-state device may perform multi-analyte assays such that the level of a target, e.g.

protein, antibodies or autoantibodies in a sample isolated from the patient may be determined in parallel with the level of a further biomarker of interest in the sample. In this context, the substrate may be one that is used conventionally in multi-analyte microarray technologies. It may, for example, be a biochip, glass slide or other conventional planar support material. The substrate may be defined as a Discrete Test Area (DTA), which defines the whole substrate, e.g. a single biochips a DTA. FIGS. 2 and 3 depict 9 DTAs and 4 DTAs respectively. Discrete Test Areas are physically distinct areas between which liquid or sample flow is not possible. Within each DTA, there may be a plurality of Discrete Test Regions (DTRs) present. These define discrete locations on a substrate and support binding agents. FIGS. 6 and 7 depict a single biochip with 2 and 4 DTRs respectively. Each DTR is spatially separated from other DTRs, and each may be used for the same or different reactions, depending on how the reactions are to be performed. The DTRs are usually present within a "biochip", and multiple biochips may be present on the device, each biochip being physically separated from other biochips. In this embodiment, the solid-state device has a multiplicity of DTRs each bearing a desired antibody covalently bound to the substrate, and in which the surface of the substrate between the DTRs is inert with respect to the target under-study. The solid-state, multi-analyte device may therefore exhibit little or no non-specific binding. Different biological molecules may be located in spatially separate locations i.e. within DTRs on the DTA or biochip. In a particular example, the DTA is approximately 1 cm$^2$ and there may be 4×4 DTRs present within each DTA, preferably 5×5 DTRs, 7×7 DTRs, 8×8 DTRs, 9×9 DTRs, 10×10 DTRs, 12×12 DTRs, 15×15 DTRs, 20×20 DTRs, 30×30 DTRs or greater present within each DTA.

A device that may be used in the invention may be prepared by activating the surface of a suitable substrate, and applying an array of probes on to discrete sites on the surface. If desired, the other active areas may be blocked. The ligands may be bound to the substrate via a linker. In particular, it is preferred that the activated surface is activated using an organosilane or polymer coating before reaction with the binding agent. The solid-state device used in the methods of the present invention may be manufactured according to the method disclosed in, for example, GB-A-2324866 the contents of which is incorporated herein in its entirety. Preferably, the solid-state device used in the methods of the present invention is the Biochip Array Technology system (BAT) (available from Randox Laboratories Limited). More preferably, the Evidence Evolution, Evidence Investigator and Multistat apparatus (available from Randox Laboratories) may be used to determine the levels of biomarkers in the sample.

The capture antibody and/or the detection antibody of the method can be selected to bind to an epitope of a target which has no glycosylation potential and which can also be sufficiently distant from a site within the target which has glycosylation potential. This ensures efficient binding by capture and detection antibodies of unglycosylated targets and can also prevent possible interference during lectin-glycan binding.

Immunoglobulin molecules are known to bear specific glycosylation modifications in the Fc portion which vary across subtype and host species. When used as an immunoassay capture molecule, such glycosylations may interfere with detection by sugar-binding reagents such as lectins by contributing to non-specific background signal. For example, fucosylation, which is a common and prominent form of immunoglobulin glycosylation, may interfere with assays using AAL lectin aimed at detecting fucose-modified biomarkers. Accordingly, strategies have been developed to obviate interference arising from capture antibody glycosylation. Firstly, use of antibody fragments such as Fab fragments, recombinant single chain variable fragments (scFvs) or single chain antibodies not containing glycosylation sites may be employed as replacements for glycosylated whole capture molecules. Alternatively, strategies may be employed in the pretreatment of capture molecules aimed at removing glycans including deglycosylase enzymes such as PNGase F, neuraminidase, mannosidase, o-glycosidase or chemical methods such as sodium periodate or phenyl boronate treatment reactive to diols which are a specific feature of many sugar structures but do not occur in proteins. Using such deglycosylation methods, interference from capture antibody glycans can be eliminated.

Accordingly, in a preferred embodiment, a portion of the patient sample is treated to remove glycols from molecules in the patient sample. The treated (deglycosylated) sample is then assayed for target (e.g. protein) content, to help calibrate the other reaction results.

The invention is further described with reference to the following non-limiting examples:

EXAMPLES

Example 1

Figure 10:
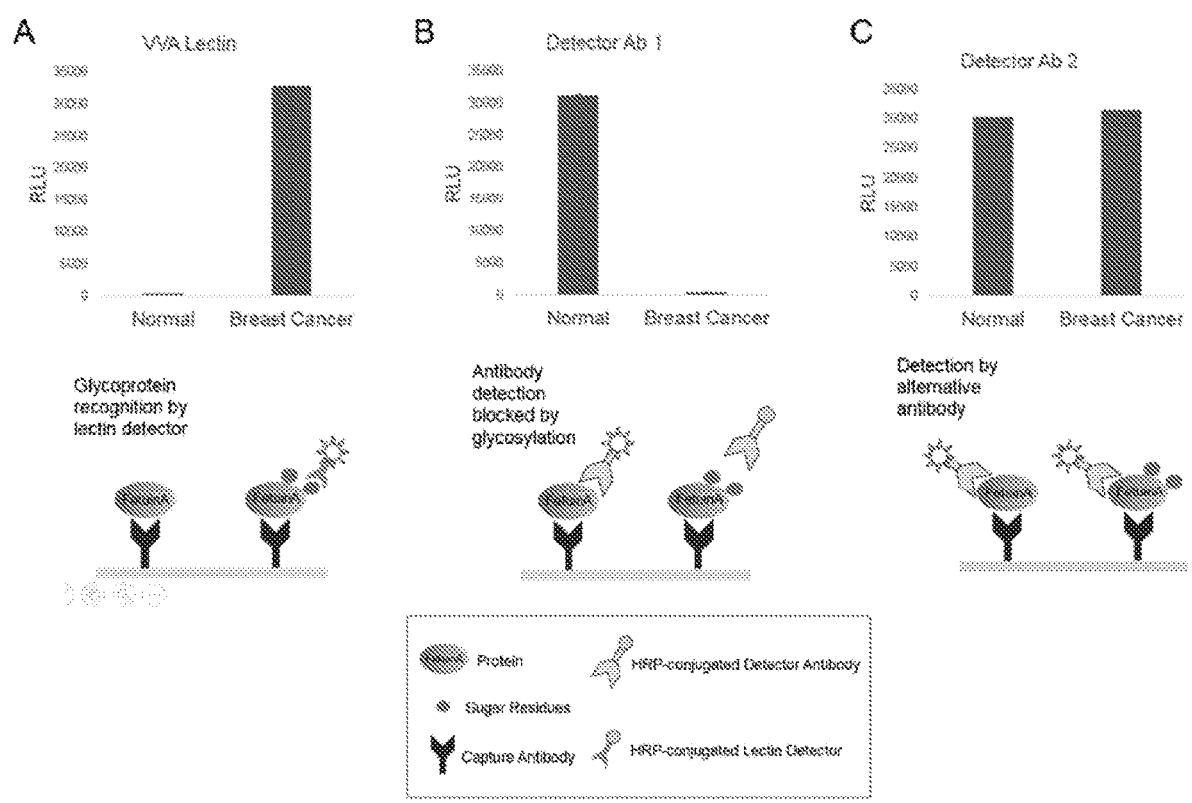
FIG. 10 shows using Vica Villosa Agglutinin (VVA) lectin, that n-aceylgalactosamine-containing fetuin A protein was detectable and indeed elevated in patients with breast cancer over normal controls. Immunoassay-based detection of captured fetuin A by two different detector antibodies (B) Ab1 and (C) Ab2 show detection of fetuin A protein was inhibited for Ab1 but not Ab2 indicative of masking of Ab1 epitope binding.

Enhanced Biomarker Detection Using Lectin/Antibody Epitope Masking by Glycosylation Fetuin A Detection Using Lectins and Antibodies Fetuin A is an acute phase anti-inflammatory glycoprotein secreted into the circulation by the liver and has been identified as a mediator of growth signalling in breast cancer cells. There are a reported six glycosylation sites on fetuin A with four O-linked n-acetylgalactosamine sites towards the protein C-terminus. The potential for these glycosylation modifications for masking the detection of captured fetuin A in serum from normal or breast cancer patients was assessed. FIG. 10 shows, using VVA lectin, that n-aceylgalactosamine-containing fetuin A protein was detectable and indeed elevated in patients with breast cancer over normal controls. However, detection of fetuin A total protein was inhibited using one particular detector antibody (termed Ab1, FIG. 10B), but not an alternative detector (Ab2, FIG. 10C) which detected similar levels of protein across the sample groups. It may be hypothesised that protein glycosylation may therefore inhibit the binding of certain detection reagents. The inhibition of protein detection by diverse glycosylation status has the potential to return erroneous results, not only in the context of immunoassays, but also potentially in proteomics-based biomarker identification.

Example 2

Figure 11:
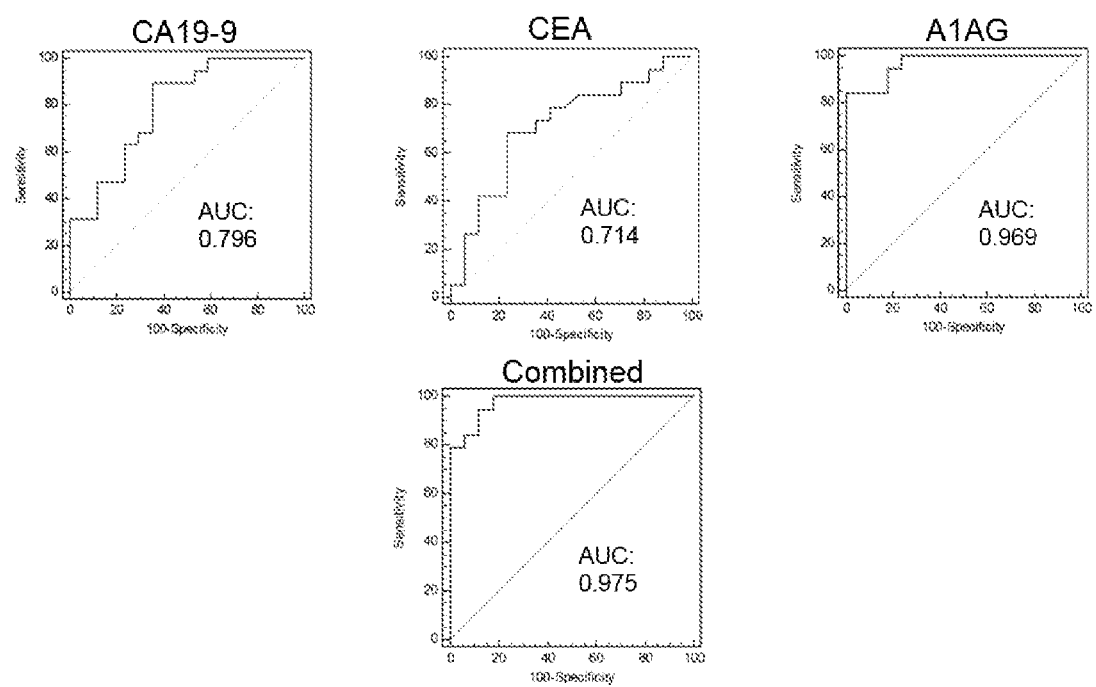
FIG. 11 shows cumulative ROC analyses (pancreatic cancer serum samples versus controls) of three fucosylated pancreatic cancer biomarkers using Aleuria Aurantia Lectin (AAL) Lectin. In a multiplexed assay context, simultaneously performed assays analysed cumulatively using logistical regression methodology results in a superior diagnostic power compared with each of the biomarkers alone.

Principle of Added Benefit Derived from Multiplexed Analysis of Glycoprotein Markers Detection by single circulating disease biomarkers for pancreatic cancer has proven inadequate due to poor identification of patients with early disease. Accordingly, the idea that a multifaceted pathology may be reflected in simultaneous detection of multiple disease markers has arisen. Proof of principle of improved diagnostic power for pancreatic cancer (pancreatic cancer serum samples versus controls) through simultaneous assessment of multiplex glycoprotein tumour markers is provided in FIG. 11 where a combined logistical regression of three analytes provides a superior ROC AUC value than either CA19-9, CEA or A1AG analysed separately.

Example 3

Examples of Added Clinical Benefit of Glycosylation

Figure 12:
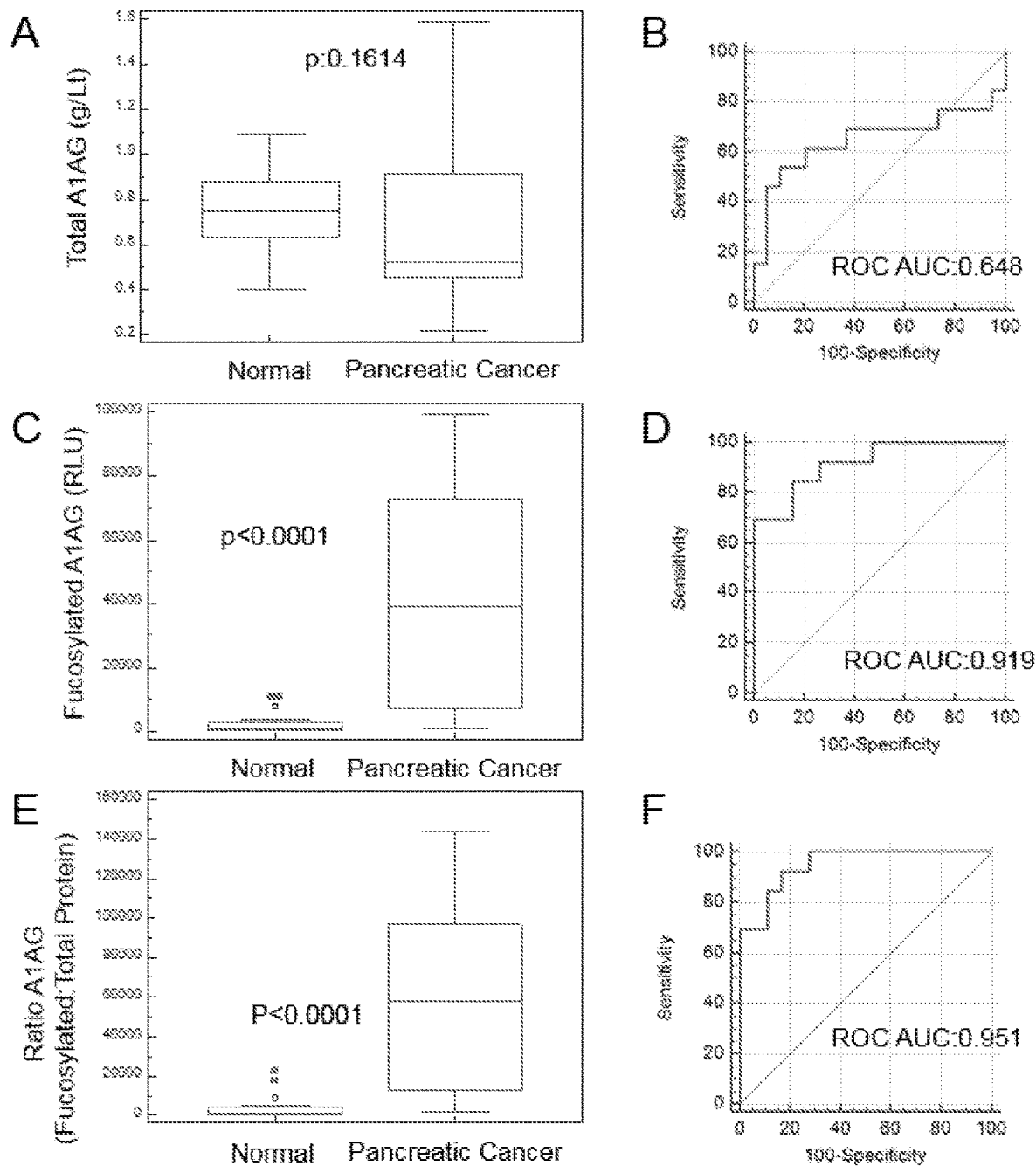
FIG. 12 shows enhanced identification of Pancreatic Cancer through detection of fucosylated Alpha 1-acid glycoprotein (A1AG) by comparison with total protein. (A) Mann Whitney statistical comparison and (B) ROC curve analyses of A1AG total protein by immunoturbidometric analysis reveal no statistically significant identification of pancreatic cancer serum samples from normal controls. In contrast, biochip-based A1AG capture followed by fucosylation detection by AAL lectin reveals a clear identification of pancreatic cancer sera by (C) ROC curve (AUC:0.919) and (D) Mann Whitney analyses (p<0.0001). (E,F) An analysis of fucosylation signal as a ratio of total protein reveals a further enhancement of the ROC curve AUC (0.951).

Improved Detection of Pancreatic Cancer Biomarkers in Patient Serum Samples Using Glycosylation A comparison of a classic immunoturbimetric total protein and biochip-based glycosylated alpha-1 acid glycoprotein (A1AG) detection was performed. Subsequent analyses were used to determine the diagnostic power of each assay platform in the identification of pancreatic cancer in a development patient sample cohort. The total protein detection method returned a ROC AUC value of 0.648 which did not reach statistical significance (p:0.2155, FIG. 12A). In addition, there was no statistical difference in total protein overall between the pancreatic cancer and normal control groups (p:0.1614, FIG. 12B). However, using AAL-mediated detection of fucosylated A1AG, a marked improvement in ROC output was observed (0.919) that reached statistical significance (p<0.0001, FIG. 12C). The RLU output representative of fucosylated A1AG also showed a significant difference between the pancreatic cancer and normal groups highlighting the addition sensitivity and clinical benefit of the biochip-based glycoprotein detection method in cancer identification. A further enhancement of diagnostic power is observed when the A1AG glycosylation signal is expressed as a ratio of total protein (FIG. 12E,F) with an evident enhancement of ROC AUC (0.951).

Example 4

Figure 13:
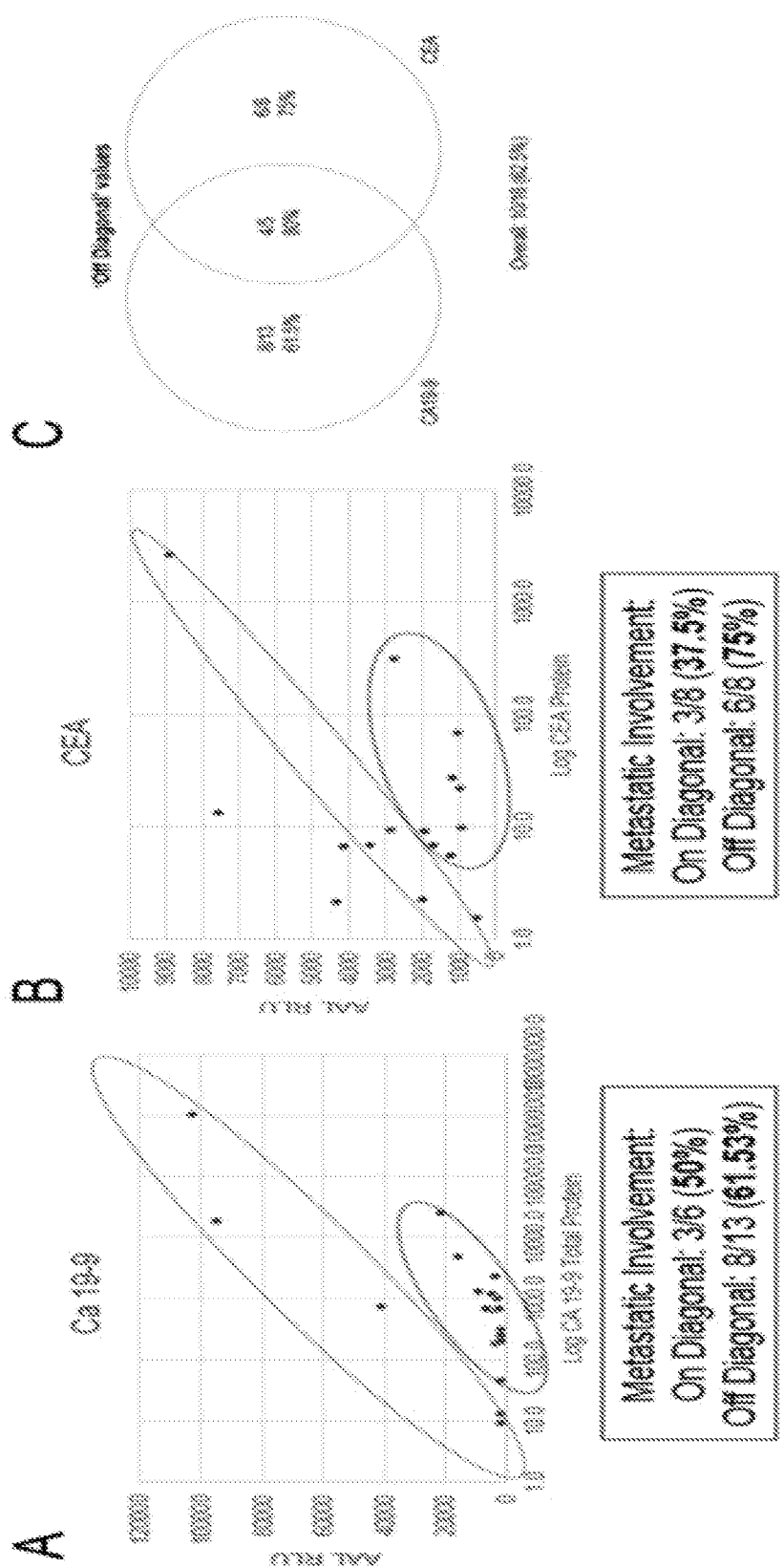
FIG. 13 shows differential glycosylation analyses of CA19-9 and CEA in pancreatic cancer serum. Using AAL lectin-based fucosylation detection, populations of hypoglycosylated CA19-9 (A) and CEA (B) were identified showing 10% and 50% increases in metastatic involvement respectively, Taken cumulatively (C), analysis of glycosylation status relative to total antigen may be predictive of metastatic involvement.

Differential Cancer Marker Glycosylation as an Indicator of Metastatic Involvement As aberrant protein glycosylation may be indicative of cancer status as tumour cells divert their sugar metabolism from protein glycosylation towards a higher metabolically active and consumptive state. The hypothesis that differential biomarker glycosylation was therefore assessed for CA19-9 and CEA. In FIG. 13, plotting fucosylation revealed by AAL lectin binding against the total protein measured, a population of hypoglycosylated protein (highlighted by the lower right ellipse in A and B) was identified in which a poor correlation was observed between glycosylation signal and total protein concentration. An increase in metastatic involvement is observed in patients with hypoglycosylated biomarkers suggesting that analysis of differential protein glycosylation may provide information on disease progression.

The invention claimed is:

1. A method of determining the level of a target biological molecule in a sample obtained from a patient, said method comprising the steps of:
(a) contacting the sample with an immobilized capture antibody that binds specifically to the target, said immobilized antibody being present at a plurality of discrete areas on a substrate or on separate substrates;
(b) at least one of said discrete areas or substrates contacting the target bound to the immobilized capture antibody with a detection antibody that specifically binds the target;
(c) at a discrete area or substrate different to that of (b), contacting the target bound to the immobilized capture antibody with a glycan-binding agent;
(d) measuring the level of the target bound by the detection antibody in (b);
(e) measuring the level of the target bound by the glycan-binding agent in (c);
(f) at a discrete area or substrate different to that of (b) or (c), contacting the sample with a capture protein immobilized on the substrate, wherein the capture protein is of the same type as the target;
(g) measuring the level of autoantibodies in the sample that bind to the capture protein via a detectable label;
(h) at a discrete area or substrate different to that of (b), (c) or (f), contacting the sample with one or more capture glycans immobilized on the substrate; and
(i) measuring the level of autoantibodies in the sample that bind to the capture glycan(s) via a detectable label,
wherein results from (b) and (c) are compared to a deglycosylated sample to thereby determine whether there is an under detection of the target due to an interfering presence of glycosylation and results from (d) and (e) are further compared to results from (f)) and (h) to assess the extent to which the under-detection of the target is compromised by the presence of autoantibodies in the sample to obtain an interfering result,
wherein the interfering result is used to recalibrate the level of (d),
wherein the target is a protein and wherein steps (a), (f) and (h), or steps (b), (c), (g) and (i), are carried out at the same time.

2. A method according to claim 1, wherein steps (b) and (c) are carried out on a single discrete test region of an assay substrate, or are carried out on physically separate reaction areas.

3. A method according to claim 1, wherein the antibody that specifically binds the target in (b) and one or more of the glycan-binding agents in (c) are detected using the same reporter molecule, and wherein the reactions (b) and (c) are carried out in physically separated reaction sites.

4. A method according to claim 1, further comprising the steps of (h) contacting the sample with one or more capture glycans immobilized on the substrate and (i) measuring the level of autoantibodies in the sample that bind to the capture glycan (s).

5. A method according to claim 4, wherein steps (a) and (h), and optionally also (f), are carried out at the same time, or wherein steps (b), (c) and (i), and optionally also (g), are carried out at the same time.

6. A method according to claim 5, wherein steps (h) and (i), are carried out in a physically separate reaction site compared to that for step (b).

7. A method according to claim 1, wherein either or both the capture antibody and detection antibody is specific for an unglycosylated site on the target.

8. A method according to claim 1, wherein the target biological molecule being measured is selected from the group consisting of monoamine oxidase B (MAO-B), tropomyosin, coagulation factor XIII, Apolipoprotein E (APOE), Glutathione S-transferase Omega-1 (GSTO-1), P-Selectin, L-selectin, E-selectin, Monocyte chemotactic protein 1 (MCP-1), Interleukin-1α (IL-1α), Interleukin-1β (IL-1β), Interleukin-8 (IL-8), Interferon-α (IFN-α), Vascular Endothelial growth factor (VEGF), Endothelial growth factor (EGF), afamin, alpha-1-antichymotrypsin, alpha-2-macroglobulin, Apolipoprotein B100 (APOB100), complement C3, complement C5, TANK binding kinase 1 (TBK-1), vitamin D binding protein, alpha-1-B glycoprotein, hemopexin, serum albumin, ceruloplasmin, alpha 2 antiplasmin, apolipoprotein A1, complement factor H, Immunoglobulin G (IgG), Immunoglobulin G Fc binding protein, hornerin, fibrinogen, Carcinoembryonic antigen (CEA), Neutrophil gelatinase-associated lipocalin (NGAL), Neuron specific enolase (NSE), Interleukin-2 (IL-2), Thrombomodulin (TM), D-dimer, Matrix Metallopeptidase 9 (MMP9), MMP9/NGAL complex, Fas ligand, C-reactive protein (CRP), Nuclear Matrix Protein 22 (NMP22), Bladder Tumour Antigen (BTA), Cytokeratin 18 (CK-18), Interleukin-1 (IL-1), Tumour Necrosis Factor α (TNFα), Soluble tumour necrosis factor receptor 1 (sTNFr1), Soluble tumour necrosis factor receptor 2 (sTNFr1), Free Prostate-Specific Antigen (FPSA), Total Prostate-Specific Antigen (TPSA), Hyaluronidase (HA), Interleukin-10 (IL-10), von Willebrand Factor (vWF), Factor VII, Nicotinamide Phosphoribosyltransferase (NAMPT), Intercellular adhesion molecule 1 (ICAM-1), Vascular Cell Adhesion Molecule 1 (VCAM-1), Fatty acid-binding protein 1 (FABP1), Fatty acid-binding protein 2 (FABP2), Fatty acid-binding protein 3 (FABP3), Fatty acid-binding protein 4 (FABP4), Fatty acid-binding protein 5 (FABP5), Fatty acid-binding protein 6 (FABP6), Fatty acid-binding protein 7 (FABP7), Fatty acid-binding protein 8 (FABP8), Fatty acid-binding protein 9 (FABP9), Glial Fibrillary Acidic Protein (GFAP), S100 calcium binding protein A10 (S100A10), S100 calcium binding protein A11 (S100A11), Interleukin-18 (IL-18), Interleukin-1 receptor antagonist (IL1-ra), α-Glutamyl transpeptidase (α-GT), Aspartate transaminase (AST), Cystatin C (CysC), C3aDesArg, troponin T (TnT), troponin I (TnI), Macrophage Inflammatory Protein 1α (MIP-1α), Adiponectin, Cluster of Differentiation 26 (CD26), GMCSF, Interleukin-15 (IL-15), Interleukin-5 (IL-5), soluble interleukin 2α (sIL-2α), soluble interleukin 6 receptor (sIL-6r), pyruvate kinase isozyme type M2 (M2-PK), secretory leukocyte proteinase inhibitor (SLPI), Prostate-specific antigen (PSA), BRCA1, BRCA2, Cluster of Differentiation 15 (CD15), Cluster of Differentiation 20 (CD20), Cluster of Differentiation 30 (CD30), Cluster of Differentiation 45 (CD45), Human epidermal growth factor receptor 2 (HER-2), brain natriuretic peptide (Pro-BNP), glycogen phosphorylase BB (GPBB), myoglobin, aspartate transaminase (AST), lactate dehydrogenase (LDH), and creatine kinase (CK).

9. A method according to claim 1, wherein the target biological molecule is selected from the list consisting of CEA, and A1AG.

10. A method according to claim 9, wherein CEA, and A1AG measurements are utilised in any combination or wherein the CEA and A1AG glycosylation measurements are used in any combination.

11. A method according to claim 10, wherein the glycosylation measurement is fucosylation.

12. A method according to claim 1, wherein glycosylated and total target measurements are compared to identity differential glycosylation states.

13. A method according to claim 12, wherein aberrant glycosylation is detected, thereby indicating the risk or presence of a disease.

14. A method according to claim 13, wherein the disease is a metastatic disease.

* * * * *